US006315566B1

(12) United States Patent
Shen et al.

(10) Patent No.: US 6,315,566 B1
(45) Date of Patent: *Nov. 13, 2001

(54) DENTAL MATERIALS

(75) Inventors: Byron Ciping Shen, Woodbury; Sumita B. Mitra, West St. Paul; Xiaodong Zhang, Woodbury; Robert D. Kuehn, Eagan, all of MN (US)

(73) Assignee: 3M Innovative Properties Company, St. Paul, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/314,491

(22) Filed: May 18, 1999

(51) Int. Cl.$^7$ ..................................... A61C 5/04

(52) U.S. Cl. .............. 433/226; 106/35; 523/116

(58) Field of Search .............. 433/226; 106/35; 523/115, 116, 118

(56) References Cited

U.S. PATENT DOCUMENTS

| | | |
|---|---|---|
| 3,655,605 | 4/1972 | Smith . |
| 3,814,717 | 6/1974 | Wilson et al. . |
| 4,143,018 | 3/1979 | Crisp et al. . |
| 4,144,324 | 3/1979 | Crutchfield et al. . |
| 4,208,401 | 6/1980 | Bauman . |
| 4,209,434 | 6/1980 | Wilson et al. . |
| 4,360,605 | 11/1982 | Schmitt et al. . |
| 4,376,835 | 3/1983 | Schmitt et al. . |
| 4,383,052 | 5/1983 | Higo et al. . |
| 4,394,494 | 7/1983 | Miyake et al. . |
| 4,407,761 | 10/1983 | Blum et al. . |
| 4,503,169 | 3/1985 | Randklev . |
| 4,639,338 | 1/1987 | Stahl et al. . |
| 4,695,251 | 9/1987 | Randklev . |
| 4,732,998 | 3/1988 | Binderup . |
| 4,877,401 | 10/1989 | Higuchi et al. . |
| 4,877,603 | 10/1989 | Degenhardt et al. . |
| 5,015,180 | 5/1991 | Randklev . |

(List continued on next page.)

FOREIGN PATENT DOCUMENTS

| | | |
|---|---|---|
| WO 97/18791 | 5/1997 | (WO) . |
| WO 97/18792 | 5/1997 | (WO) . |
| WO 98/43596 | 10/1998 | (WO) . |
| WO 98/46197 | 10/1998 | (WO) . |
| WO 99/03444 | 1/1999 | (WO) . |

OTHER PUBLICATIONS

Y. Imai et al., "Preparation and Properties of Hydrophilic Methacrylate Monomers," *New Functionality Materials, vol. B, Synthesis and Function Control of Biofunctionality Materials*, 1993, p. 43.

Simmelink, J.W., "Ultrastructural Effects of Diphosphonates on Dental Enamel," *Adv. Dent. Res.*, vol. 1 No. 2, Dec. 1987, p. 356.

Anbar, M. et al., "Potential Use of Organic Polyphosphonates as Adhesives in the Restoration of Teeth," *J. Dent. Res.*, vol. 53 No. 4, Jul.–Aug. 1974, p. 879.

Anbar, M. et al., "Improved Adhesion of Acrylic Restorative Materials to Dental Enamel by Precoating with Monomers Containing Phosphonate Groups," *J. Dent. Res.*, vol. 56, No. 8, Aug. 1977, p. 943.

Anbar, M. et al., "Organic Polymeric Polyphosphonates as Potential Preventive Agents of Dental Caries: In Vitro Experiments," *J. Dent. Res.*, vol. 53, No. 4, Jul.–Aug. 1974, p. 867.

Anbar, M. et al., "Organic Polymeric Polyphosphonates as Potential Preventive Agents of Dental Caries: In Vitro Experiments," *J. Dent. Res.*, vol. 53, No. 5, Sep.–Oct. 1974, p. 1240.

Anbar, M. et al., "Adsorption of Polyphosphonated Polyethylene on Enamel of Teeth," *J. Dent. Res.*, vol. 50, No. 3, May–Jun. 1971, p. 778.

Saunders, J.H. and Frisch, K.C., *Polyurethanes Chemistry and Technology*, Part I., Chemistry, 1962, pp. 73–75, 80–81.

www.sigma–aldrich.com/sacatalog.nsf/ProductLookup/Aldrich436909?Open Document—printed May 2, 2001 (Exhibit A).

www.sigma–aldrich.com/sacatalog.nsf/StructForm?OpenForm&ParentUNID=3B74D04CB826 978086256A2200757A7F—printed May 2, 2001 (Exhibit B).

Davy, K.W.M., et al. "Relationship Between Composite Matrix Molecular Structure and Properties", Biomaterials 19 (1998) 2007–2014.

*Primary Examiner*—John J. Wilson
*Assistant Examiner*—Melba Bumgarner

(57) ABSTRACT

Dental materials are provided comprising Component i), which is a hydrogen bondable compound that is a polymer having a molecular weight greater than about 10,000, and Component ii), which is a hydrogen bondable bridging compound. One of Components i) and ii) contains 2 or more hydrogen-bond donor sites per compound, and the other of Components i) or ii) contains 2 or more hydrogen-bond acceptor sites per compound, which hydrogen-bond acceptor sites are not capable of also acting as hydrogen-bond donor sites. Components i) and ii) are present in an amount sufficient to exhibit at least 10% higher Relative Viscosity, and optionally at least one of i) or ii) is polymerizable. If the material contains any compounds having only one hydrogen-bond donor site or hydrogen-bond acceptor site per compound, the ratio of hydrogen-bond donor sites on compounds having only one hydrogen-bond donor site to hydrogen-bond donor sites on compounds having 2 or more hydrogen-bond donor sites per compound is less than 0.25, and the ratio of hydrogen-bond acceptor sites on compounds having only one hydrogen-bond acceptor site to hydrogen-bond acceptor sites on compounds having 2 or more hydrogen-bond acceptor sites per compound is less than 0.25.

18 Claims, No Drawings

U.S. PATENT DOCUMENTS

| | | |
|---|---|---|
| 5,019,651 | 5/1991 | Kieczykowski . |
| 5,096,699 | 3/1992 | Gaffar et al. . |
| 5,130,347 | 7/1992 | Mitra . |
| 5,162,310 | 11/1992 | Jaeggi . |
| 5,204,426 | 4/1993 | Ellis et al. . |
| 5,208,009 | 5/1993 | Gaffar et al. . |
| 5,218,070 | 6/1993 | Blackwell . |
| 5,258,067 | 11/1993 | Podszun et al. . |
| 5,260,483 | 11/1993 | Davis et al. . |
| 5,270,365 | 12/1993 | Gertz et al. . |
| 5,332,429 | 7/1994 | Mitra et al. . |
| 5,354,199 | 10/1994 | Jacobs et al. . |
| 5,441,945 | 8/1995 | Yoshikawa . |
| 5,444,104 * | 8/1995 | Waknine ............................... 522/24 |
| 5,451,401 | 9/1995 | Zerby et al. . |
| 5,520,725 * | 5/1996 | Kato et al. ............................. 106/35 |
| 5,525,648 | 6/1996 | Aasen et al. . |
| 5,547,379 | 8/1996 | Hasel . |
| 5,652,227 | 7/1997 | Teronen et al. . |
| 5,665,120 | 9/1997 | Ohtsuka et al. . |
| 5,965,632 * | 10/1999 | Orlowski et al. ..................... 523/116 |

* cited by examiner

DENTAL MATERIALS

FIELD OF THE INVENTION

The present invention relates to dental compositions. More specifically, the present invention relates to compositions that have unique handling properties for use in the dental arts in the treatment of teeth.

BACKGROUND OF THE INVENTION

Dental materials comprising resin and, in certain circumstances, filler, are used as restorative materials to repair tooth structure, or as sealants or adhesives. These materials are applied in an uncured state, and then cured in the mouth, often by exposure to a curing light that initiates a polymerization reaction. The consistency of the materials when first applied in an uncured state may be problematic in that they may flow more than desired. This is particularly the case for adhesives or sealants, which may tend to flow in an uncontrolled manner. More highly filled materials, in the category of dental restoratives, tend to exhibit a slower flow characteristic called "slump." Slump may be a problem because the shape imparted to the dental material may change in the time between shaping by the practitioner and polymerization of the material by exposure to light.

Certain restoratives, particularly those for materials that are to be used as posterior composites, are designed to be of particularly high viscosity. Ideally, a resin based material would be formulated such that it mimics the placement characteristics of amalgam filling materials, which are condensed in the mouth by packing. During this packing process, the amalgam condenses such that it will displace a matrix band, a thin metal strip that acts as a form for the restoration and assures appropriate contact of the restoration with adjacent dentition. The current art in achieving the desired packable viscosity of resin based products uses higher filler loading and/or fillers with beneficial sizes and shapes. The problem associated with this approach is that those materials often appear dry and tend to be crumbly when handled. Another approach is to increase resin viscosity to create heavy body material. The material from this approach may be too sticky for optimal use, and also may be dry and crumbly.

SUMMARY OF THE INVENTION

Dental materials are provided that exhibit unique handling characteristics based on the hydrogen bonding properties of components of the material. More specifically, dental materials are provided comprising Component i), which is a hydrogen bondable compound that is a polymer having a molecular weight greater than about 10,000, and Component ii), which is a hydrogen bondable bridging compound. One of Components i) and ii) contains 2 or more hydrogen-bond donor sites per compound, and the other of Components i) or ii) contains 2 or more hydrogen-bond acceptor sites per compound, which hydrogen-bond acceptor sites are not capable of also acting as hydrogen-bond donor sites. Components i) and ii) are present in an amount sufficient to exhibit at least 10% higher Relative Viscosity, and optionally at least one of i) or ii) is polymerizable. If the material contains any additional compounds having only one hydrogen-bond donor site or hydrogen-bond acceptor site per compound, the ratio of hydrogen-bond donor sites on compounds having only one hydrogen-bond donor site to hydrogen-bond donor sites on compounds having 2 or more hydrogen-bond donor sites per compound is less than 0.25, and the ratio of hydrogen-bond acceptor sites on compounds having only one hydrogen-bond acceptor site to hydrogen-bond acceptor sites on compounds having 2 or more hydrogen-bond acceptor sites per compound is less than 0.25.

For purposes of the present invention, the term "compound" means any chemical entity, including monomer, oligomer, polymer or filler particle.

"Relative Viscosity," for purposes of the present invention, is a comparison of a subject composition, which is an uncured desired composition of the present invention, with the viscosity of a comparative composition that is identical in composition to the subject composition except that the hydrogen bond donor sites have been functionalized so that they are no longer capable of donating hydrogen. For example, hydrogen bond donor sites that are hydroxy functionalities may be functionalized by reacting with acetic anhydride or acetyl chloride to form the ester or acetate. The appropriate functionalization to perform this evaluation is selected based on the ability to carry out the reaction with the compound, while adding only the additional chemical entity necessary to eliminate the hydrogen donor sites. It is contemplated that functionalization to form acetate esters or methyl or ethyl ethers or their equivalents depending on the starting hydrogen bond donor sites will provide appropriate comparisons to show the effect of the hydrogen bond interaction between Components i) and ii).

The present invention provides unique handling characteristics over a broad spectrum of dental material classes. The specific class of dental materials selected for preparation by the artisan is determined by incorporation of ingredients specific to that class of materials, or otherwise formulating to provide the specific physical property characteristic required for that class, such as initial viscosity. Thus, improved properties may be observed for dental restoratives that are in the categories as defined herein as packable, shapeable or flowable composites, as well as for less viscous dental materials such as sealants and adhesives.

DETAILED DESCRIPTION OF THE INVENTION

A novel method of modifying and controlling the rheology of dental materials, and particularly those for dental composite materials, has been developed utilizing hydrogen bonding between materials that act as hydrogen-bond acceptors and materials that act as hydrogen-bond donors. Without being bound by theory, it is believed that the selection of the specific components as described herein provides for creation of a hydrogen bonded matrix when the material is in the uncured state. This matrix exhibits unusual structural behavior when the material is undisturbed or when force is applied to a large surface of the material. However, the material exhibits dramatically different rheological properties when the material is under bulk or localized shear force. Thus, the material will tend to stay where it is desired to stay due to the presence of the hydrogen bonded matrix, and will move easily when it is desirable to do so simply by applying force in a manner that disrupts the hydrogen bonded matrix.

Using this novel approach, we have created dental materials that have excellent rheological properties beneficial to the handling and ease-of-use aspects of dental procedures. In one aspect of the present invention, the rheology of dental composite material (i.e. dental restorative materials made from polymerizable components and filler materials) are significantly improved as compared to prior dental composite materials.

In one embodiment of the present invention, dental composites may exhibit heavy body characteristics that offer a "packable" composite. A "packable" composite is a material that can be placed in the cavity and which when compressed by a dental probe will exert enough lateral force to distort a matrix band and additionally will tend to hold the matrix band out essentially in this distorted position after the dental probe has been removed from the composite material. Preferably, the packable material is defined as a material having a 2.5 kg Consistency Value as described herein between 9.5 mm and 28 mm and a Placement Force Value as described herein between 400 and 1200 grams.

Most preferably, composites of the present invention will exhibit an unusual behavior in that it will exhibit an ability to be formed in the shape of an arch as defined by the Arch Test described herein, and will hold that position without slumping or deformation.

The non-slumping and non-sticky characteristics make the material easy to handle and manipulate. Composites of the present invention also may be sculpted and shaped to create anatomy on the occlusal surface, thereby saving time in the finishing and polishing step.

The present invention provides great flexibility in determining the overall composition of the dental material, because the rheology of the composition is controlled by changing the ratio of hydrogen-bond acceptor to hydrogen-bond donor materials, as well as adjusting the resin viscosity, and the filler loading.

Thus, a dental composite may be formulated in accordance with the present invention that is highly featherable. Featherability is the ability to spread a material from a thick layer to a thin layer without causing tearing or roughness of the surface of the material. This property is important, because the dental practitioner generally applies composite as a relatively thick quantity of material, and manipulates that material with dental instruments to the desired shape. If the spreading of the composite material results in torn or rough surfaces, more time is required to smooth these surfaces to the necessary final appearance. Such additional final finishing time is both expensive as well as uncomfortable for the patient.

Preferred embodiments of the present invention include dental composites that are not "packable," but which have improved rheological properties, including reduced slump. Such restoratives will be generally referred to in this description for convenience of reference only as "shapeable," even though "packable" and "flowable" composites are also mechanically shapeable. The "shapeable" composites of the present invention are preferred over composites of the prior art because they exhibit excellent handling properties without slump, and also may be formulated such that they do not stick to dental instruments.

The present invention also contemplates a "flowable" composite, which is a filled dental restorative material that can be dispensed from a syringe or other storage container having a relatively small exit orifice. Preferably, the flowable composite of the present invention is dispensable from a 1 cc syringe (main body dimensions are 6.17 mm internal diameter, 56.77 mm long, and a tip diameter of 1.96 mm and length of 8.0 mm) having a 20 gauge hypodermic needle by applying less than 2.5 kg of pressure thereto in a crosshead speed of 2 mm/min., yet is sufficiently resistant to flow in a static system such that a 500 mg sample will not flow from a vertical glass surface.

All of the composite materials of the present invention, whether packable, shapeable or flowable, preferably include the class of dental composites that are fluoride releasing materials, such as those referred to as "compomers," or similar hybrid systems.

Additional alternative embodiments of the present invention include materials that have lower viscosity, such as dental adhesives and sealants. These compositions may be filled or unfilled. These compositions do not flow once located on the desired substrate, yet are easily extruded or dispensed from the storage container and are easily spread about the desired substrate when subjected to an application force, such as from a brush, sponge or other applicator.

An additional particularly preferred embodiment of the present invention is orthodontic adhesives. This type of adhesive generally has a 1 kg Consistency Value between 23 and 32 mm and surprisingly has sufficient body to hold an unsupported bracket or band on a tooth for a long time before cure. This embodiment is particularly preferred as a precoated bracket, i.e. a bracket that comes from the factory with adhesive already adhered thereto. Preferably such a bracket would be applied to a surface, such as, the bottom of a package, using the uncured adhesive coated on the bracket as the fixative. Orthodontic adhesives according to the present invention will not extrude or squeeze out from beneath the bracket due to the weight of the bracket. Precoated brackets are disclosed in U.S. Pat. Nos. 5,015,180 and 5,354,199, which are hereby incorporated by reference.

As an additional embodiment of the present invention, the dental material may be provided as a two-part formulation, wherein Component i) is provided in the first part (part A), and Component ii) is provided in the second part (part B). Upon mixing of parts A and B, the dental material exhibits significantly higher viscosity than either part individually. This provides for easy dispensing and handling of the dental material, with excellent high viscosity handling properties upon mixing. Parts A and B may be provided in separate containers, or in separate sides of a multiple barrel syringe optionally fitted with a static mixing device. Parts A and B may thus be automatically mixed on dispensing through a static mixing device, or may optionally be mixed by the user through another appropriate technique, such as hand spatulation.

The two part system may optionally be provided with a photopolymerization initiator system, or alternatively may be provided with a two part chemical (e.g. "dark") cure system that initiates polymerization upon mixing of the parts of the polymerization system.

Components i) and ii) of the present materials contain either hydrogen-bond donor or acceptor sites. Hydrogen-bond acceptor sites are preferably selected such that they have greater affinity for coordination with active hydrogen than the hydrogen-bond donor sites of the other compounds in the material. Thus, while hydrogen-bond donor sites all have the capability of coordinating with other hydrogen-bond donor functionalities, hydrogen-bond acceptor sites in accordance with the present invention do not contain hydrogen. The hydrogen-bond donor sites therefore preferentially coordinate with the hydrogen-bond acceptor sites.

Preferred hydrogen-bond acceptor sites include nitrogen-containing compounds that do not contain an active hydrogen on the nitrogen. Examples of such functionalities include amides (RR'NC(O)R" where R and R' are not H, such as N-alkyl acrylamides and N-alkyl methacrylamides), vinyl azalactones, tertiary amine functionalities, quaternary ammonium cations having alkyl groups on N, and suitable heterocycles such as pyridines, pyrrolidones and oxazolines.

Hydrogen-bond donor sites are functionalities containing active hydrogen that is readily coordinated with a hydrogen-bond acceptor site. Preferred hydrogen-bond donor sites are hydroxy, primary or secondary amines, acids, S-H functionalities and N-H functionalities in amides, urethanes, and urea groups.

As noted above, the dental materials of the present invention comprises a Component i), which is a hydrogen bondable compound that is a polymer having a molecular weight greater than about 10,000. More preferably, the polymer has a molecular weight greater than about 20,000, and most preferably greater than about 50,000. Preferably, the polymer has a molecular weight between about 50,000 and 250,000. Generally, this component need not be present in great amounts in the compositions of the present invention. Preferably, Component i) is present as about 0.05–8% of the resin component of the present invention, and more preferably as about 0.1–5% of the resin component of the present invention.

Preferably, Component i) comprises hydrogen-bond acceptor sites. Particularly preferred Component i) compounds are poly(N-vinylpyrrolidone) polymers ("p-NVP"). Copolymers of vinylpyrrolidone and other monomers or grafted poly(N-vinylpyrrolidone) with other groups also are preferred, provided that the co-monomers or grafting groups do not contain an adverse amount of active hydrogens for hydrogen bonding. For example, poly(1-vinylpyrrolidone-co-styrene), poly(1-vinylpyrrolidone-co-vinyl acetate), and so on, are preferred. By prudent selection of co-monomers, one may control or modify the solubility of copolymer(s) in a given resin formulation. Other preferred Component i) compounds are poly(vinyl acetamide) and polyethyloxazoline.

The dental materials of the present invention also comprise a Component ii), which is a hydrogen bondable bridging compound. Preferably Component ii) is present as 30%–60% by weight of the resin component. Thus, Component ii) may optionally be a monomer, oligomer, polymer or filler particle. Most preferably, Component ii) is a monomer or filler particle. When Component ii) is a monomer, the hydrogen-bonding sites are preferably spaced at least about 9 angstroms apart in order to provide effective bridging. More preferably, the hydrogen-bonding sites are spaced by a sterically rigid moiety, so that the spacing is physically maintained in the resin system of the dental material. Most preferably, the hydrogen-bonding sites are spaced by one or more cyclic moieties, and particularly by one or more aromatic moieties. Component ii) is a monomer or filler particle. When Component ii) is a monomer, the hydrogen-bonding sites are preferably spaced at least about 9 angstroms apart in order to provide effective bridging. More preferably, the hydrogen-bonding sites are spaced by a sterically rigid moiety, so that the spacing is physically maintained in the resin system of the dental material. Most preferably, the hydrogen-bonding sites are spaced by one or more cyclic moieties, and particularly by one or more aromatic moieties.

Examples of preferred materials for use as Component ii) of the resin include the diglycidyl methacrylate of bisphenol A ("BisGMA"); diurethanedimethacrylate ("DUDMA," such as CAS No. 41137-60-4, commercially available as ROHAMERE 6661-0 from Rohm Tech, Inc. (Malden, MA)); 2,2'bis(4-acryloxyphenyl)propane; 2,2'-bis[4(2-hydroxy-3-methacryloxy-phenyl)]propane; 2,2'-bis[3(4-phenoxy)-2-hydroxypropane-1-methacrylate]propane; 2,2'-bis[3(4-phenoxy)-2-hydroxypropane-1-acrylate]propane; di-2-methacryloyloxethyl hexamethylene dicarbamate; di-2-methacryloxyethyl trimethylhexanethylene dicarbamate; di-2-methacryloyl oxyethyl dimethylbenzene dicarbamate; methylene-bis-2-methacryloxyethyl-4-cyclohexyl carbamate; di-2-methacryloxyethyl-dimethylcyclohexane dicarbamate; methylene-bis-2-methacryloxyethyl-4-cyclohexyl carbamate; di-1-methyl-2-methacryloxyethyl-trimethyl-hexamethylene dicarbamate; di-1-methyl-2-methacryloxyethyl-dimethylbenzene dicarbamate; di-1-methyl-2-methacryloxyethyl-dimethylcyclohexane dicarbamate; methylene-bis-1-methyl-2-methacryloxyethyl-4-cyclohexyl carbamate; di-1-chloromethyl-2-methacryloxyethyl-hexamethylene dicarbamate; di-1-chloromethyl-2-methacryloxyethyl-trimethylhexanethylene dicarbamate; di-1-chloromethyl-2-methacryloxyethyl-dimethylbenzene dicarbamate; di-1-chloromethyl-2-methacryloxyethyl-dimethylcyclohexane dicarbamate; methylene-bis-2-methacryloxyethyl-4-cyclohexyl carbamate; di-1-methyl-2-methacryloxyethyl-hexamethylene dicarbamate; di-1-methyl-2-methacryloxyethyl-trimethylhexamethylene dicarbamate; di-1-methyl-2-methacryloxyethyl-dimethylbenzene dicarbamate; di-1-methyl-2-methacryloxyethyl-dimethylcyclohexane dicarbamate; methylene-bis-1-methyl-2-methacryloxyethyl-4 -cyclohexyl carbamate; di-b 1-chloromethyl-2-methacryloxyethyl-hexamethylene dicarbamate; di-1-chloromethyl-2-methacryloxyethyl-dimethylbenzene dicarbamate; di-1-chloromethyl-2-methacryloxyethyl -dimethylbenzene dicarbamate; di-1-chloromethyl-2-methacryloxyethyl-dimethylcyclohexane dicarbamate; methylene-bis-1-chloromethyl-2-methacryloxyethyl-4-cyclohexyl carbamate; and the like.

Alternatively, Component ii) may be a polymer. In the case of hydrogen-bond donor compounds, the Component ii) preferably may be selected from polyvinyl alcohol, and copolymers of polyvinyl alcohol with other functionalities. Alternative polymers include polymers having carboxy functionalities, such as polycarboxylic acid and copolymers of itaconic acid and acrylic acid.

In yet another alternative, Component ii) may be a functionalized filler particle having either hydrogen-bond acceptor or donor functionality, as appropriate. For example, colloidal silica (e.g., fumed silica) comprises a significant number of hydroxyl functionalities, and acts as an excellent bridging compound together with p-NVP polymer. Colloidal silica may be present as 1–100% by weight of the total filler to act as an effective component ii) material. Surprisingly, a small amount of a functionalized filler may perform the function of bridging compound in the present invention. Thus even amounts as low as 1–10% of the overall filler will exhibit the desired effect. Colloidal silica may be optionally silane treated.

Compounds having both acceptor and donor functionalities may be used, but are generally less desirable because they tend to coordinate with themselves.

The resin of the present invention may additionally contain a component iii), which are compounds that comprise only one hydrogen-bond donor site. These compounds may be present in only limited quantities because they will compete for the hydrogen-bonding sites of Component i) or ii), which results in less physical hydrogen bond bridging in the resin matrix. Addition of a small amount of such materials may be used beneficially as another method to modify rheology and fine tune the desired handling characteristics. Resin materials that have a single hydrogen-bond donor functionality and which are polymerizable include 2-hydroxyethyl acrylate, 2-hydroxyethyl methacrylate ("HEMA"), hydroxypropyl acrylate, hydroxypropyl methacrylate, glycerol di-acrylate, glycerol di-methacrylate, and polyethylene glycol mono methacrylate polypropylene glycol mono methacrylate, and the like.

Compositions of the present invention preferably contain non-hydrogen bonding compounds that may be said to act as diluents for the hydrogen bonding aspect of the present invention. For purposes of the present invention, a diluent or polymerizable diluent may be one chemical entity or a mixture of two or more chemical entities. Preferably, these diluent compounds are polymerizable, so that they are part of the cured matrix of the ultimate product in the mouth. These diluents typically are of lower viscosity, so that they enable formulation of the appropriate uncured material for the desired end use and act as solvents to enable incorporation of all components in a relatively homogeneous manner. The class of diluents as described for purposes of the present invention may additionally comprise functionalities that do not contribute to the hydrogen bonding aspect of the present invention, but which provide some other beneficial property to the dental material. Preferably, the polymerizable diluent is present as 36–69.8% by weight of the resin component.

Preferred examples of diluents in accordance with the present invention include triethyleneglycol dimethacrylate ("TEGDMA"), polyethylene glycol dimethacrylate ("PEGDMA") and 2,2'-bis(4-methacryloxy(ethoxy)$_n$phenyl)propane (wherein n=1–5) ("BisEMA").

Additional examples of diluents are methyl acrylate; methyl methacrylate; ethyl acrylate; ethyl methacrylate; propyl acrylate; propyl methacrylate; isopropyl acrylate; isopropyl methacrylate; tetrahydrofurfuryl acrylate; tetrahydrofurfuryl methacrylate; glycidyl acrylate; glycidyl methacrylate; ethyleneglycol diacrylate, ethyleneglycol dimethacrylate; polyethyleneglycol diacrylate (where the number of repeating ethylene oxide units vary from 2 to 30); polyethyleneglycol dimethacrylate (where the number of repeating ethylene oxide units vary from 2 to 30); neopentyl glycol diacrylate; neopentylglycol dimethacrylate; trimethylolpropane triacrylate; trimethylol propane trimethacrylate; tetra- acrylates and methacrylates of pentaerythiitol and dipentaerythritol; 1,3-butanediol diacrylate; 1,3-butanediol dimethacrylate; 1,4-butanedioldiacrylate; 1,4-butanediol dimethacrylate; 1,6-hexane diol diacrylate; 1,6-hexanediol dimethacrylate;

One embodiment of the present invention is compositions specifically designed to additionally utilize a cement reaction as an additional curing mode of the compositions. These compositions incorporate reactive fillers that react with acid functionality present in the resin portion of the composition in the presence of water to undergo a cement reaction. The reactive filler may or may not have the property of releasing fluoride. Such fillers include those that are commonly used with ionomers to form ionomer cements. Examples of suitable reactive fillers include metal oxides such as zinc oxide and magnesium oxide, and ion-leachable glasses, e.g., as described in U.S. Pat. Nos. 3,655,605; 3,814,717; 4,143,018; 4,209,434; 4,360,605 and 4,376,835. Such reactive fillers may be incorporated to modify the handling characteristics or to affect the setting properties of the ultimate composition. Compositions that have a sufficient amount of reactive filler to undergo the cement reaction are generally less tolerant of the presence of water in the uncured state, because the cement reaction prematurely begins before use by the practitioner when water is present. Preferably, compositions containing reactive filler are substantially free of added water.

The reactive filler is preferably a finely divided reactive filler. The filler should be sufficiently finely-divided so that it can be conveniently mixed with the other ingredients and used in the mouth. Preferred average particle diameters for the filler are about 0.2 to about 15 microns, more preferably about 1 to 10 microns, as measured using, for example, a sedimentation analyzer.

Suitable acid-reactive fillers include metal oxides, metal salts and glasses. Preferred metal oxides include barium oxide, calcium oxide, magnesium oxide and zinc oxide. Preferred metal salts include salts of multivalent cations, for example aluminum acetate, aluminum chloride, calcium chloride, magnesium chloride, zinc chloride, aluminum nitrate, barium nitrate, calcium nitrate, magnesium nitrate, strontium nitrate and calcium fluoroborate. Preferred glasses include borate glasses, phosphate glasses and fluoroaluminosilicate glasses.

Most preferred of the acid reactive fillers are those that release fluoride. Fluoride releasing glasses, in addition to providing good handling and final composition properties as discussed above, provide the benefit of long-term release of fluoride in use, for example in the oral cavity. Fluoroaluminosilicate glasses are particularly preferred. Suitable acid reactive fillers are also available from a variety of commercial sources familiar to those skilled in the art. For example, suitable fillers can be obtained from a number of commercially available glass ionomer cements. Mixtures of fillers can be used if desired.

If desired, the acid reactive filler can be subjected to a surface treatment. Suitable surface treatments include acid washing, treatment with phosphates, treatment with chelating agents such as tartaric acid, treatment with a silane coupling agent or silanol coupling agent. Particularly preferred acid reactive fillers are silanol treated fluoroaluminosilicate glass fillers, as described in U.S. Pat. No. 5,332,429, the disclosure of which is expressly incorporated by reference herein.

Non-acid reactive fillers may be selected from one or more of any material suitable for incorporation in compositions used for medical applications, such as fillers currently used in dental restorative compositions and the like. The filler is finely divided and preferably has a maximum particle diameter less than about 10 microns and an average particle diameter less than about 1.0 microns. More preferably, the filler has a maximum particle diameter less than about 1.0 microns and an average particle size of diameter less than about 0.1 microns. The filler can have a unimodal or polymodal (e.g., bimodal) particle size distribution. The filler can be an inorganic material. It can also be a crosslinked organic material that is insoluble in the polymerizable resin, and is optionally filled with inorganic filler. The filler should in any event be non-toxic and suitable for use in the mouth. The filler can be radiopaque or non-radiopaque.

Examples of suitable non-acid reactive inorganic fillers are naturally-occurring or synthetic materials such as quartz, nitrides (e.g., silicon nitride), glasses derived from, for example Ce, Sb, Sn, Zr, Sr, Ba and Al, colloidal silica, feldspar, borosilicate glass, kaolin, talc, titania, and zinc glass; low Mohs hardness fillers such as those described in U.S. Pat. No. 4,695,251; and submicron silica particles (e.g., pyrogenic silicas such as the "Aerosil" Series "OX 50", "130", "150" and "200" silicas sold by Degussa and "Cab-O-Sil M5" silica sold by Cabot Corp.). Examples of suitable non-reactive organic filler particles include filled or unfilled pulverized polycarbonates, polyepoxides, polyacrylics, and the like. Preferred non-acid reactive filler particles are quartz, submicron silica, and non-vitreous microparticles of the type described in U.S. Pat. No. 4,503,169. Mixtures of these non-acid reactive fillers are also contemplated, as well as combination fillers made from organic and inorganic materials.

Preferably the surface of the filler particles is treated with a coupling agent in order to enhance the bond between the filler and the polymerizable resin. The use of suitable coupling agents include gamma methacryloxypropyltrimethoxysilane, gamma-mercaptopropyltriethoxysilane, gamma-aminopropyltrimethoxysilane, and the like.

If desired, the compositions of the invention can contain adjuvants such as cosolvents, pigments, inhibitors, accelerators, stabilizers, viscosity modifiers, surfactants, rheology modifiers, colorants, medicaments and other ingredients that will be apparent to those skilled in the art.

In another aspect of the present invention, manufacture of dental restorative compositions of the present invention is made easier by use of specific process steps. In many situations, a heavy body material is desired but is often difficult to manufacture (e.g., difficulties with mixing and extrusion)) and package (e.g., filling syringes) due to the high viscosity. This problem may be circumvented by either adding one or the other of Components i) or ii) (for example, p-NVP) in the form of solid powder during mixing. Alternatively, Component i) or ii) may be pre-dispersed onto the surface of fillers before mixing. Using this process, the viscosity of the material is kept at a relatively lower level during manufacturing process. After the material comes out of the manufacturing and packaging processes, as the solid Component i) or ii) gradually dissolves into the resin matrix, the viscosity of the material builds up over time to the desired level.

In order to demonstrate the non-slumping characteristics of the inventive paste, a simple "Arch" test was developed. In this evaluation, a thin strand of paste is shaped into an arch. The longer the arch remains standing up with no slumping or deformation, the better it is in its non-slumping attribute. More specifically, the paste materials to be tested are filled into standard dental restorative capsules having exit orifices of about 2 mm. Paste is then extruded from the capsule as a thin strand of approximately 2 mm in diameter and 2 cm in length. The strand of paste is shaped like an arch with both ends of the arch attached to a glass plate (the strand now resembles an inchworm standing up on the glass plate) 1 cm apart. The test can be carried out either at room temperature (approximately 22° C.) or at elevated temperatures, e.g., 37° C. The time that the arch remains standing with no slumping or deformation indicates how good the material is in its non-slumping attribute. Preferably, the arch retains its shape at room temperature for more than one hour. More preferably, the arch retains its shape at 37° C. for more than one hour.

In the aspect of the present invention related to composites, the present invention provides a non-slumping material. Because the material of the present invention in essence "stays where you put it," dentists do not have to overfill the cavity, as currently required for runnier commercially available materials. The present invention also provides a material that is more easily manipulated to adapt to the margins, and later, to sculpted to create anatomy on the occlusal surface. The inventive material thus enables the dental professional to save time and material in the restoration procedure, especially in the margin adaptation and the finishing/polishing steps.

The dental composites of the present invention further exhibit a creamy, shiny appearance that is desirable for aesthetics of the ultimate restoration. This appearance cannot be obtained in materials that achieve packability or low slump characteristics through high filler loading.

The viscosity of flowable and shapable dental materials of the present invention is determined using a parallel plate, rheometer (model ARES, Rheometric Scientific, N.J.) having a 0.5 mm gap and plates having a 25 mm diameter. The frequency of the rheometer is 0.1 radians/sec. with a strain of 200%. Adjustments of the set up parameters of viscosity measurement for other materials of the present invention having either very low viscosity or very high viscosity are made as apparent to those knowledgeable in the viscosity measurement art. Thus, specific measurement parameters may be required to measure the viscosity of a material of a given viscosity range. The specific viscosity measurement values of these other materials are not critical, however their Relative Viscosity as compared to materials that are not of the present invention will be appreciated by the skilled artisan regardless of the specific measurement technique.

EXAMPLES

The following examples are provided for purposes of illustrating the present invention, and are not intended to be limiting of the broadest concepts of the present invention. Unless otherwise indicated, all parts and percentages are by weight and all molecular weights are weight average molecular weight.

Testing Procedures

All of the following tests were performed at room temperature, approximately 22° C.

Test A

Consistency Value

The Consistency Value was conducted using the following procedure: A cylindrical sample of paste (1 cm in diameter, 0.7 cm in height, approximately 1.2 g in weight) was placed on a square glass plate, 10×10×5 mm. A glass plate, 10×10×5 mm, weighing 115 g was then placed on top of the paste sample to be tested. An additional steel or brass cylinder weight was placed atop the top plate. The total weight placed, including the top glass plate and cylinder weight, on top of the cylindrical paste sample equaled 1 kg or 2.5 kg. The diameter of the circle resulting from flattening or compressing the paste with the weight was measured after two minutes when using the 1 kg of weight or four minutes when using the 2.5 kg weight. The circular diameter of the flattened cylinder of paste was measured and recorded as the "Consistency Value in mm."

Test B

Placement Force Value

Force required to place a dental restoration of the present invention in a cavity was evaluated by the following procedure:

A sample was placed in a QTS25 Texture Analyzer (Stevens Mechtric, United Kingdom). This instrument moves a cylindrical, stainless steel, flat-headed probe (Part No. TA39), 2 mm in diameter and 20 mm in length, into the test sample (Teflon™ cup having 20 mm diameter and 6.5 mm depth, filled with paste) at a speed of 70 mm/min for a total travel length of 2 mm. The instrument reports the peak resistance that is encountered during the travel of the probe head.

Test C

Drip Test for Low Filler Loaded Pastes.

A small amount of paste, approximately 33 mg, was placed on a vertically positioned microscope glass slide. The distance that the paste moved down the glass slide after a one-minute period was measured and recorded. For more viscous pastes, samples up to 500 mg, a time period of up to five minutes can be used.

Below is a list abbreviations used in the examples.

BISEMA6 ethoxylated (6 mole ethylene oxide) bisphenol A dimethacrylate (Sartomer CD541, Union Carbide), BHT, 2,6-Di-tert-butyl-4-methylphenol PDMA, 2,2-di(N-methacryloxyethyl carbamoylmethyl) propionic acid TEGDMA, Triethyleneglycol dimethacrylate DUDMA—Diurethane dimethacrylate, CAS No. 41137-60-4, which is commercially available as Rohamere 6661-0 from Rohm Tech, Inc. (Malden, Mass.)

p-NVP, poly(N-vinyl pyrrolidone) (38,000 MW)

EDMAB, Ethyl 4-dimethylaminobenzoate

BisGMA, 2,2-bis[4-(2-hydroxy-3-methacryloyloxy-propoxy)phenyl]propane

DPI PF6, Diphenyl lodonium Hexafluorophosphate

CPQ, Camphorquinone

GDMA, Glycerol dimethacrylate

Tinuvin- P, 2-(2H-Benzotriazol-2-yl)-4-methylphenol (Ciba-Geigy)

Preparatory Filler Example 1

A sol-gel derived filler was prepared as follows: 25.5 parts silica sol ("Ludox" LS: E. I. DuPont de Nemours & Co.) were acidified by the rapid addition of 0.255 parts concentrated nitric acid. In a separate vessel, 12.9 parts ion-exchanged zirconyl acetate (Magnesium Elektron, Inc.) were diluted with 20 parts deionized water and the resultant solution acidified with 0.255 parts concentrated nitric acid. The silica sol was pumped into the stirred zirconyl acetate solution and mixed for one hour. The stirred mixture was filtered through a 3 mm filter followed by a 1 mm filter. The filtrate was poured into trays to a depth of about 25 mm and dried at 65° C. in a forced air oven for about 35 hours (hrs). The resultant dried material was removed from the oven and tumbled through a rotary tube furnace (Harper Furnace Corp.), which was preheated to 950° C. The calcined material was comminuted in a tumbling ball mill with ¼" alumina media until an average particle size of 0.5–1.2 micron (as measured on a Micromeritics 5100 sedigraph) was achieved. The mill charge included 75 parts calcined material, 3 parts methanol, 1.9 parts benzoic acid, and 1.1 parts deionized water. The filler was then loaded into ceramic saggers and fired in an electric furnace (L&L Furnace Corp.) in air at 880–900° C. for approximately 8 hrs. The fired filler was then ball-milled for 4–5 hrs. The mill charge included 32 parts fired filler, 1.25 parts ethanol, and 0.3 parts deionized water. Next, the filler was passed through a 74 mm nylon screen in a vibratory screener (Vortisiv V/S 10010). The filler was then blended in a V-blender (Patterson-Kelly Corp.) for about 15 min.

Silane treatment was as follows: 32 parts by weight (pbw) of the filler was added to 48.94 pbw of deionized water under vigorous stirring. Trifluoroacetic acid (TFAA), 0.104 pbw, was added slowly. The pH was then adjusted to 3.0–3.3. by adding further 5 pbw increments of TFAA. Then, 3.56 pbw of silane A-174 (Inc,) was added. The slurry was stirred for about 2 hours, poured into a tray lined with a plastic sheet, and then dried in an oven set at 90° C. for 13 hours. The cakes of dried filler were crushed and passed through a 74 um screen.

Preparatory Filler Example 2

Treated Fumed Silica (OX-50) was made as follows: a solution of 3312 g MeOH and 720 g deionized water was premixed for 1 minute. Glacial Acetic Acid, 1024 g, was slowly added to the water followed by 4968 g A-174 silane. The above solution was mixed for 1 hour. At the end of the hydrolysis step, the solution was clear. The solution was used within 30 minutes after hydrolysis. The above solution and 20700 g OX-50 powder were blended for approximately 40 minutes and the treated filler was immediately discharged into drying trays, and was dried at 67° C. for 3.75 hours and then another 1.25 hours at 100° C. The dried filler was screened through a 74 mm nylon screen in a vibratory screener (Vortisiv V/S 10010).

Preparatory Example—Preparation of PDMA

Bis(hydroxymethyl)propionic acid di(N-methacryloxyethyl)carbamate (PDMA) is synthesized by reacting 2,2-Bis(hydroxymethyl)propionic acid (BHMPA) and two equivalents of Isocyanatoethylmethacrylate (IEM) as follows 2,2-Bis(hydroxymethyl)propionic acid (BHMPA, 225.21 g, 1.679 mole), small amounts of stabilizer(s) such as 2,6-Di-tert-butyl-4-methylphenol (BHT, 1.6781 g, 7.615 mmole) and/or Triphenyl antimony (TPS, 1.3463 g, 3.813 mmole), and a catalytic amount of Dibutlytin dilaurate (2.4396 g, 3.863 mmole) and dry THF or other suitable solvents were added first to the reactor. After the solution was stirred for a short while, IEM (592.64 g, 3.823 mole) was added. The reaction was heated to 65° C. for about 30 hours while stirring constantly. The solvent was stripped off after the conversion was completed. The final product, PDMA, was a colorless, viscous liquid.

Flowable Compositions

Example 1

30 pbw of the following resin components were mixed with 70 pbw of the Preparatory Filler Example 1.

TABLE 1

| Resin Components | Ratio | Pbw |
|---|---|---|
| p-NVP |  | 2.00 |
| PDMA/TEGDMA | 85/15 | 8.82 |
| UDMA |  | 25.05 |
| TEGDMA |  | 31.98 |
| BisGMA/TEGDMA | 90/10 | 30.30 |
| EDMAB |  | 1.00 |
| BHT |  | 0.10 |
| DPI PF6 |  | 0.50 |
| CPQ |  | 0.25 |
| Total |  | 100.0 |

Comparative Example 2

30 pbw of the following resin components were mixed with 70 pbw of the Preparatory Filler Example.

TABLE 2

| Components | pbw |
|---|---|
| EDMAB | 0.01 |
| CPQ | 0.0017 |
| Tinuvin-P | 0.01 |

TABLE 2-continued

| Components | pbw |
|---|---|
| DPI PF6 | 0.006 |
| BisGMA | 48.62 |
| TEGDMA | 48.62 |

TABLE 3

Test C
Drip Test

| Example No. | Weight of sample (g) | Distance moved by sample (mm) |
|---|---|---|
| Example 1 | 0.033 | 0 |
| Comparative Example 2 | 0.033 | 13.8 |

Example 1, containing PDMA, did not move during the one-minute test.

Examples 3–5

Examples 3 through 5 were made mixing the resin components as listed in Table 4 under standard conditions. Then 18.2 pbw of each resin was then mixed with 81.8 pbw of the Preparatory Filler Example 1. Consistency Values for the resulting pastes, Table 5, were collected by using the 1 kg of total weight and 2 minute duration of Test Procedure A.

TABLE 4

| Resin Components for | p-NVP | GDMA | TEGDMA | BisGMA/ TEGDMA 90/10 | EDMAB | BHT | DPI PF6 | CPQ |
|---|---|---|---|---|---|---|---|---|
| Comparative Example 3 | 0 | 0 | 43.15 | 55 | 1 | 0.1 | 0.5 | 0.25 |
| Example 4 | 1.34 | 4 | 37.82 | 55 | 1 | 0.1 | 0.5 | 0.25 |
| Example 5 | 2 | 6 | 35.15 | 55 | 1 | 0.1 | 0.5 | 0.25 |

TABLE 5

Consistency Values (mm)

| Paste Example No. | Test Procedure A @ 1 kg of weight for 2 min |
|---|---|
| Comparative Example 3 | 47.6 |
| Example 4 | 40.5 |
| Example 5 | 11.9 |

Example series 3–5 shows that incorporation of p-NVP significantly decreases the Consistency Value of the paste, even with the addition of GDMA, a compound having only one hydrogen bond donor site. GDMA is incorporated in this system to assist in compatibilzing the p-NVP. It is expected that compositions using a non-hydrogen bond donor compound to assist in solubilization will exhibit even greater effects on the rheology of the paste.

Example 6

Two resin formulations, with and without poly (ethyloxazoline) (MW 200,000) instead of p-NVP as the hydrogen bondable polymer, were made combining the components listed in Table 6. The viscosity of each of the resin examples, Table 7, was measured using a controlled strain rheometer (model Ares, Rheometric Scientific, NJ). The resin samples were placed in between two parallel plates (25 mm diameter) at a gap of 0.5 mm and were evaluated at a frequency of 0.1 radians/sec. and a strain rate of 200%.

TABLE 6

| Resin | RESIN A Pbw | Comparative RESIN B Pbw |
|---|---|---|
| BisGMA | 49 | 50 |
| TEGDMA | 49 | 50 |
| Poly(ethyloxazoline) | 0.5 | 0 |
| GDMA | 1.5 | 0 |

TABLE 7

| | Viscosity Pa-s | |
|---|---|---|
| | RESIN A | Comparative RESIN B |
| Resin | BisGMA/TEGDMA | BisGMA/TEGDMA |
| % poly(ethyloxazoline) | 0.5 | 0 |
| Viscosity (Pa-s) | $8.40 \times 10^4$ | $3.01 \times 10^2$ |

In the BisGMA/TEGDMA OX50 system, addition of 0.5% poly(ethyloxazoline) resulted in a dramatic increase in viscosity by about 280-fold.

Example 7

Paste samples P1–P10 were prepared by starting with the resins R1–R4 shown in Table 8. Specified quantities of the polymerizable components, with or without p-NVP, were thoroughly mixed to provide resin mixtures R1–R4. Pastes P1–P8 were formulated by mixing 40 pbw of the one of the resin mixtures with 60 pbw of treated filler of Preparatory Example 1 or Preparatory Example 2 as specified in Table 10. Pastes P9 and P10 were compounded by mixing 60 pbw of resin mixture R1 or R2 with 40 pbw of untreated OX50 (Degussa).

The viscosity of each if these paste samples was measured using a controlled strain rheometer (model ARES, Rheometric Scientific, N.J.). Paste samples were placed in between two parallel plates (25 mm diameter) at a gap of 0.5 mm. Measurements of viscosity were performed at varying shear rates starting from $0.00625$ $s^{-1}$ to $1.0$ $s^{-}$ in 12 logarithmically-spaced shear rate steps. A low shear rate of $0.025$ $s^{-1}$ was used to compare the viscosity values since this condition is most representative of the clinical situation. Table 9 summarizes the viscosity values of Examples 7a–7j.

TABLE 8

| Resin | BisGMA | BisEMA6 | TEGDMA | p-NVP | GDMA |
|---|---|---|---|---|---|
| Comparative R1 | 50 | 0 | 50 | 0 | 0 |
| R2 | 49 | 0 | 49 | 0.5 | 1.5 |
| Comparative R3 | 0 | 50 | 50 | 0 | 0 |
| R4 | 0 | 49 | 49 | 0.5 | 1.5 |

TABLE 9

| Example | Paste | Resin | Filler type | Viscosity Pa-s |
|---|---|---|---|---|
| 7a(Comparative) | P1 | R1 | Prep. Ex 1 | 6.6* |
| 7b | P2 | R2 | Prep. Ex 1 | $1.43 \times 10^3$ |
| 7c(Comparative) | P3 | R3 | Prep. Ex 1 | 2.7* |
| 7d | P4 | R4 | Prep. Ex 1 | $3.97 \times 10^2$ |
| 7e(Comparative) | P5 | R1 | Prep. Ex 2 | $3.01 \times 10^2$ |
| 7f | P6 | R2 | Prep. Ex 2 | $4.46 \times 10^4$ |
| 7g(Comparative) | P7 | R3 | Prep. Ex 2 | $9.14 \times 10^3$ |
| 7h | P8 | R4 | Prep. Ex 2 | $8.40 \times 10^4$ |
| 7i(Comparative) | P9 | R1 | Untreated OX50 | 17 |
| 7j | P10 | R2 | Untreated OX50 | $1.24 \times 10^5$ |

In the examples above, the increase in viscosity is quite dramatic when a small amount of p-NVP forms a component of the paste, illustrating the effect of hydrogen bonding interaction between the p-NVP and the donor sites. For pastes 7c, 7d, 7g and 7h, the donor sites are being provided by the treated filler surface. For the other six pastes, the resin as well as the treated filler are providing the donor sites. Comparison of 7f and 7j shows that the effect of the donor properties of the filler surface is more dramatic for the untreated filler vs. the treated filler.

What is claimed is:

1. A dental material comprising 10% to 40% by weight resin and 60% to 90% by weight filler, wherein the resin comprises:
    0.05% to 8% by weight, based on the total weight of the resin, of a nitrogen-containing polymer that does not contain an active hydrogen on nitrogen;
    30% to 60% by weight, based on the total weight of the resin, of a compound that contains at least two hydroxyl groups; and
    36% to 69.8% by weight, based on the total weight of the resin, of a non-hydrogen bonding polymerizable diluent.

2. The dental material of claim 1 having a viscosity between 5,000 and 50,000 Pa-s.

3. The dental material of claim 1, which is an orthodontic adhesive having a 1 Kg Consistency Value between 23 and 32 mm.

4. The dental material of claim 1 wherein the nitrogen-containing polymer that does not contain an active hydrogen on nitrogen has a weight average molecular weight greater than about 20,000.

5. The dental material of claim 1, wherein the nitrogen-containing polymer that does not contain an active hydrogen on nitrogen has a weight average molecular weight between about 50,000 and 250,000.

6. The dental material of claim 1, wherein the nitrogen-containing polymer that does not contain an active hydrogen on nitrogen is selected from the group consisting of poly N-vinylpyrrolidone, polyvinyl acetamide, poly(1-vinylpyrrolidone-co-styrene), poly(1-vinyl pyrrolidene-co-vinyl acetate), and polyethyloxazoline.

7. The dental material of claim 1, wherein the compound that contains at least two hydroxyl groups is a filler having hydroxyl functionality.

8. The dental material of claim 1, wherein the compound that contains at least two hydroxyl groups is selected from the group consisting of Bis-GMA and polyvinyl alcohol.

9. The dental material of claim 1 further comprising a monomer, oligomer, or polymer with one hydrogen donor site.

10. The dental material of claim 9, wherein said monomer, oligomer, or polymer with one hydrogen donor site is selected from the group consisting of 2-hydroxyethyl acrylate, 2-hydroxyethyl methacrylate, hydroxypropyl acrylate, hydroxypropyl methacrylate, glycerol di-acrylate, glycerol di-methacrylate, polyethylene glycol mono methacrylate and polypropylene glycol mono methacrylate.

11. The dental material of claim 1, wherein the diluent is selected from the group consisting of polyethylene glycol dimethacrylate and 2,2'-bis(4-methacryloxy(ethoxy)$_n$phenyl)propane, where n=1 to 5.

12. A method of filling a cavity in a tooth, comprising: preparing a tooth for placement of a restorative in a cavity therein; packing a dental material of claim 2 in the cavity; and polymerizing the dental material in the cavity.

13. A method of filling a cavity in a tooth, comprising: preparing a tooth for placement of a restorative in a cavity therein; placing and shaping a dental material of claim 3 in the cavity; and polymerizing the dental material in the cavity.

14. A method of bonding an orthodontic bracket to a tooth, comprising:
    preparing a tooth for placement of an orthodontic bracket on the tooth;
    placing a bracket having an orthodontic adhesive of claim 4 disposed thereon on the tooth so that the adhesive is in contact with the tooth;
    pressing the bracket to make firm contact of the adhesive coated bracket to said tooth; and
    polymerizing the orthodontic adhesive to bond the orthodontic bracket to the tooth.

15. A dental material comprising 10% to 40% by weight resin and 60% to 90% by weight filler, wherein the resin comprises:
    a nitrogen-containing polymer that does not contain an active hydrogen on nitrogen selected from the group consisting of poly(N-vinylpyrrolidone), poly(N-vinylpyrrolidone) copolymers, poly(vinyl acetamide), polyethyloxazoline, and combinations thereof;
    a compound that contains at least two hydroxyl groups; and
    a non-hydrogen bonding polymerizable diluent.

16. A dental material comprising 10% to 40% by weight resin and 60% to 90% by weight filler, wherein the resin comprises:
    a nitrogen-containing polymer that does not contain an active hydrogen on nitrogen;
    a compound that contains at least two hydroxyl groups selected from the group consisting of diglycidyl methacrylate of bis-phenol A; 2,2'-bis[4(2-hydroxy-3-methacryloxyphenyl)]propane; 2,2'-bis[3(4-phenoxy)-2-hydroxypropane-1-methacrylate]propane; 2,2'-bis[3(4-phenoxy)-2-hydroxypropane-1-acrylate]propane; poly(vinyl alcohol); poly(vinylalcohol) copolymers; hydroxyl-functional fillers; and combinations thereof; and
    a non-hydrogen bonding polymerizable diluent.

17. A dental material comprising 10% to 40% by weight resin and 60% to 90% by weight filler, wherein the resin comprises:

a nitrogen-containing polymer that does not contain an active hydrogen on nitrogen;

a compound that contains at least two hydroxyl groups; and a non-hydrogen bonding polymerizable diluent selected from the group consisting of triethyleneglycol dimethacrylate; polyethylene glycol dimethacrylate; 2,2'-bis(4-methacryloxy(ethoxy)$_n$phenyl)propane, where n=1–5; methyl acrylate; methyl methacrylate; ethyl acrylate; ethyl methacrylate; propyl acrylate; propyl methacrylate; isopropyl acrylate; isopropyl methacrylate; tetrahydrofurfuryl acrylate; tetrahydrofurfuryl methacrylate; glycidyl acrylate; glycidyl methacrylate; ethyleneglycol diacrylate; ethyleneglycol dimethacrylate; polyethyleneglycol diacrylate; polyethyleneglycol dimethacrylate; neopentyl glycol diacrylate; neopentylglycol dimethacrylate; trimethylolpropane triacrylate; trimethylol propane trimethacrylate; tetraacrylates and methacrylates of pentaerythritol and dipentaerythritol; 1,3-butanediol diacrylate; 1,3-butanediol dimethacrylate; 1,4-butanedioldiacrylate; 1,4-butanediol dimethacrylate; 1,6-hexanediol diacrylate; 1,6-hexanediol dimethacrylate; and combinations thereof.

18. A dental material comprising 10% to 40% by weight resin and 60% to 90% by weight filler, wherein the resin comprises:

a nitrogen-containing polymer that does not contain an active hydrogen on nitrogen selected from the group consisting of poly(N-vinylpyrrolidone), poly(N-vinylpyrrolidone) copolymers, poly(vinyl acetamide), polyethyloxazoline, and combinations thereof;

a compound that contains at least two hydroxyl groups selected from the group consisting of diglycidyl methacrylate of bis-phenol A; 2,2'-bis[4(2-hydroxy-3-methacryloxyphenyl)]propane; 2,2'-bis[3(4-phenoxy)-2-hydroxypropane-1-methacrylate]propane; 2,2'-bis[3(4-phenoxy)-2-hydroxypropane-1-acrylate]propane; poly(vinyl alcohol); poly(vinylalcohol) copolymers; hydroxyl-functional fillers; and combinations thereof, and a non-hydrogen bonding polymerizable diluent selected from the group consisting of triethyleneglycol dimethacrylate; polyethylene glycol dimethacrylate; 2,2'-bis(4-methacryloxy(ethoxy)$_n$phenyl)propane, where n=1–5; methyl acrylate; methyl methacrylate; ethyl acrylate; ethyl methacrylate; propyl acrylate; propyl methacrylate; isopropyl acrylate; isopropyl methacrylate; tetrahydrofurfuryl acrylate; tetrahydrofurfuryl methacrylate; glycidyl acrylate; glycidyl methacrylate; ethyleneglycol diacrylate; ethyleneglycol dimethacrylate; polyethyleneglycol diacrylate; polyethyleneglycol dimethacrylate; neopentyl glycol diacrylate; neopentylglycol dimethacrylate; trimethylolpropane triacrylate; trimethylol propane trimethacrylate; tetraacrylates and methacrylates of pentaerythritol and dipentaerythritol; 1,3-butanediol diacrylate; 1,3-butanediol dimethacrylate; 1,4-butanedioldiacrylate; 1,4-butanediol dimethacrylate; 1,6-hexanediol diacrylate; 1,6-hexanediol dimethacrylate; and combinations thereof.

\* \* \* \* \*